(12) United States Patent
Fritsch et al.

(10) Patent No.: US 7,502,108 B2
(45) Date of Patent: Mar. 10, 2009

(54) ASSEMBLY AND METHOD FOR IDENTIFYING COATINGS LYING ON THE SURFACE OF COMPONENTS AND FOR DETERMINING THEIR CHARACTERISTICS

(75) Inventors: Manfred Fritsch, Kleinpuerschuetz (DE); Nico Correns, Weimar (DE); Felix Kerstan, Jena (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 342 days.

(21) Appl. No.: 10/559,175

(22) PCT Filed: May 21, 2004

(86) PCT No.: PCT/EP2004/005446

§ 371 (c)(1),
(2), (4) Date: Apr. 26, 2006

(87) PCT Pub. No.: WO2004/106853

PCT Pub. Date: Dec. 9, 2004

(65) Prior Publication Data

US 2007/0195323 A1    Aug. 23, 2007

(30) Foreign Application Priority Data

Jun. 3, 2003    (DE)  ................. 103 24 934

(51) Int. Cl.
*G01J 3/36*    (2006.01)
(52) U.S. Cl. ...................... 356/328; 356/326
(58) Field of Classification Search ............ 356/328
See application file for complete search history.

(56) References Cited

U.S. PATENT DOCUMENTS

| 4,544,271 | A | | 10/1985 | Yamamoto |
| 5,166,752 | A | | 11/1992 | Spanier et al. |
| 5,424,827 | A | * | 6/1995 | Horwitz et al. ............. 356/328 |
| 5,517,032 | A | | 5/1996 | Imani |
| 6,052,188 | A | | 4/2000 | Fluckiger et al. |
| 6,952,260 | B2 | * | 10/2005 | Xiao ......................... 356/326 |
| 7,167,239 | B2 | * | 1/2007 | Yamamoto ................. 356/326 |
| 7,215,422 | B2 | * | 5/2007 | Florek et al. .............. 356/328 |

FOREIGN PATENT DOCUMENTS

| DE | 44 13 758 | 12/1994 |
| DE | 195 06 550 | 8/1996 |
| DE | 196 15 366 | 10/1997 |

(Continued)

*Primary Examiner*—L. G Lauchman
(74) *Attorney, Agent, or Firm*—Reed Smith LLP

(57) ABSTRACT

The invention is directed to an arrangement for detecting coatings which are arranged on surfaces of structural component parts or objects and for determining the chemical characteristics and surface properties of these coatings. It comprises a light source for illuminating the coating to be analyzed on the surface of the structural component part and means for imaging the light source on an entrance slit over the surface of the coating to be analyzed. The entrance slit is imaged in a wavelength-dependent manner on a two-dimensional detector unit by a grating. An evaluating unit which is electrically connected to the detector unit serves to evaluate and process the signals supplied by the exposed detector elements of the detector unit.

5 Claims, 3 Drawing Sheets

FOREIGN PATENT DOCUMENTS

| | | |
|---|---|---|
| DE | 199 27 015 | 12/2000 |
| EP | 0 080 699 | 6/1983 |
| FR | 2 810 732 | 12/2001 |
| WO | WO 95/02814 | 1/1995 |
| WO | WO 99/24786 | 5/1999 |

* cited by examiner

ASSEMBLY AND METHOD FOR IDENTIFYING COATINGS LYING ON THE SURFACE OF COMPONENTS AND FOR DETERMINING THEIR CHARACTERISTICS

CROSS-REFERENCE TO RELATED APPLICATIONS

This application claims priority of International Application No. PCT/EP03/04024, filed Apr. 17, 2003, and German Application No. 102 17 543.8, filed Apr. 17, 2002, the complete disclosures of which are hereby incorporated by reference.

BACKGROUND OF THE INVENTION a) Field of the Invention

The invention is directed to an arrangement and a method for detecting coatings lying on surfaces of structural component parts and for determining the characteristics thereof, in particular of coatings of water, ice and dirt on surfaces, preferably in structural components parts of vehicles. Above all, the chemical characteristics and surface properties of the coatings, particularly the roughness, are to be determined.

b) Description of the Related Art

In order to detect such coatings on surfaces of vehicle parts of this type and to determine their characteristics, these coatings are usually irradiated or penetrated by optical radiation and the radiation which is reflected by these coatings or which passes through them is measured and evaluated in different spectral regions. The presence of coatings can be deduced from these measurements and when such coatings are present their characteristics, particularly their chemical properties, can be determined.

There are various methods and arrangements for determining the surface condition of structural component parts in vehicles.

DE 199 27 015 A1 discloses a method and a device for determining the thickness and growth rate of a coating of ice on structural component parts of aircraft, wherein the radiation impinging on a coating on the surface of the structural component part is resolved into wavelength regions by a holographic grating connected to a photoelectric line receiver and the line receiver compares the measured radiation to a stored reflection curve of the surface of the structural component part without coating. The growth rate of a coating of this kind can also be determined within a number of temporally spaced measurement intervals.

The device for carrying out the measurements has a window through which the radiation which is influenced by the surface reaches the grating via an optical imaging system and a completely illuminated entrance slit, is spectrally separated according to wavelength on the grating, and is imaged on the line receiver by the grating. The signals of the elements of the line receiver are evaluated by means of a controlling and evaluating unit which is connected to the line receiver. The results of the measurements are made visible by a display.

This method is disadvantageous due to the fact that no distinction is made between the mechanical states of these coatings. Only a sum thickness or concentration is determined. In particular, coatings of ice, snow or frost cannot be distinguished spectrographically or, if so, only in a highly uneconomical manner. The roughness of a coating cannot be determined in this way.

FR 2 810 732 A1 discloses a spectrometer with a two-dimensional detector. The signal of a plurality of detector elements which lie perpendicular to the dispersion direction of the spectrometer and which are associated with the same wavelength are summed in the two-dimensional detectors. The spectrum obtained is evaluated. CCD elements or CMOS elements are provided as detector elements.

OBJECT AND SUMMARY OF THE INVENTION

It is the primary object of the present invention to provide an arrangement and a method for detecting coatings on structural component parts and for determining the characteristics thereof by which the surface structure of coatings of this kind, in addition to the thickness and the chemical composition, can be detected in a simple manner by means of a more economical detector.

According to the invention, this object is met in an arrangement for detecting coatings that are arranged on surfaces of structural component parts and for determining the chemical characteristics and surface properties of these coatings comprises a light source for illuminating a coating to be analyzed on the surface of the structural component part, means for imaging the light source on an entrance slit over the surface of the coating to be analyzed, a grating which images the entrance slit on a two-dimensional detector unit in a wavelength-dependent manner and an evaluating unit which is electrically connected to the detector unit for evaluating and processing the signals supplied by the exposed detector elements of the detector unit.

It is advantageous when the detector arrangement comprises detector elements arranged in a matrix. These can advantageously be CCD elements or CMOS elements.

In contrast to the prior art cited above, the special nature of the arrangement according to the invention and the method implemented thereby consists in that the entrance slit is not completely illuminated by the light which is scattered or reflected by the coating, in particular by the surface of the coating. Accordingly, when there is no coating present or when a coating having a smooth surface is present on the structural component part in question, only a relatively small portion of the entrance slit is illuminated. The imaging of the slit by the imaging grating upon the extensive, two-dimensionally resolving detector arrangement allows a spectrum to be formed in the shape of a narrow stripe.

In the case of a rough surface of the coating being analyzed, the light that is no longer reflected or scattered on it in a directed manner illuminates an area of the entrance slit, which area varies in size depending upon the degree of roughness and which is imaged on the two-dimensionally resolving detector arrangement by the imaging grating. The spectrum forms on the detector arrangement in the shape of a broad stripe. The roughness, among other properties, of the coating being analyzed can be determined from the signals delivered by the detector elements that are arranged two-dimensionally.

According to a method for detecting coatings that are arranged on surfaces of structural component parts and for determining the characteristics of these coatings and their surface properties, the following method steps are carried out with the arrangement referred to above.

the coating which is located on the surface of the structural component part and which is to be analyzed is illuminated by an illumination source;

the illumination source is imaged on an entrance slit over the surface of the coating which is to be analyzed and which reflects and/or scatters the light;

the exposed entrance slit is so imaged in a wavelength-dependent manner by an imaging grating upon a two-dimensional detector unit comprising detector elements arranged in a matrix that a broader or narrower two-dimensional area of the detector unit is irradiated depending upon the properties or roughness of the surface of the coating; and the signals of the exposed detector elements of the detector unit are evaluated and the measured values pertaining to the characteristics of the analyzed coating are determined and displayed.

A portion of the slit of varying breadth (size) depending on the surface properties of the coating is illuminated by means of this imaging of the illumination source on the slit. The wavelength-dependent imaging of the illuminated portion of the entrance slit on the detector elements of the detector unit is carried out in particular by an imaging holographic grating in such a way that a two-dimensional area of the detector unit of varying breadth depending upon the roughness of the surface to be analyzed is irradiated. A spectral separation of the light influenced by the coating is also carried out by means of the holographic grating. The signals of the exposed detector elements are evaluated and the measurement values pertaining to the characteristics of the analyzed coating are evaluated and outputted in an evaluating unit.

Depending on the object to be analyzed, the illumination of the coating can advantageously be carried out with transmitted light or incident light.

Further, it is advantageous when measurement values for the roughness of the coating surface are determined from the breadth of the exposed area of the detector unit. The chemical composition of the coating, for example, can be determined from the spectral distribution.

In the following, the invention will be described in more detail with reference to an embodiment example.

DESCRIPTION OF THE PREFERRED EMBODIMENTS

Figure 1:
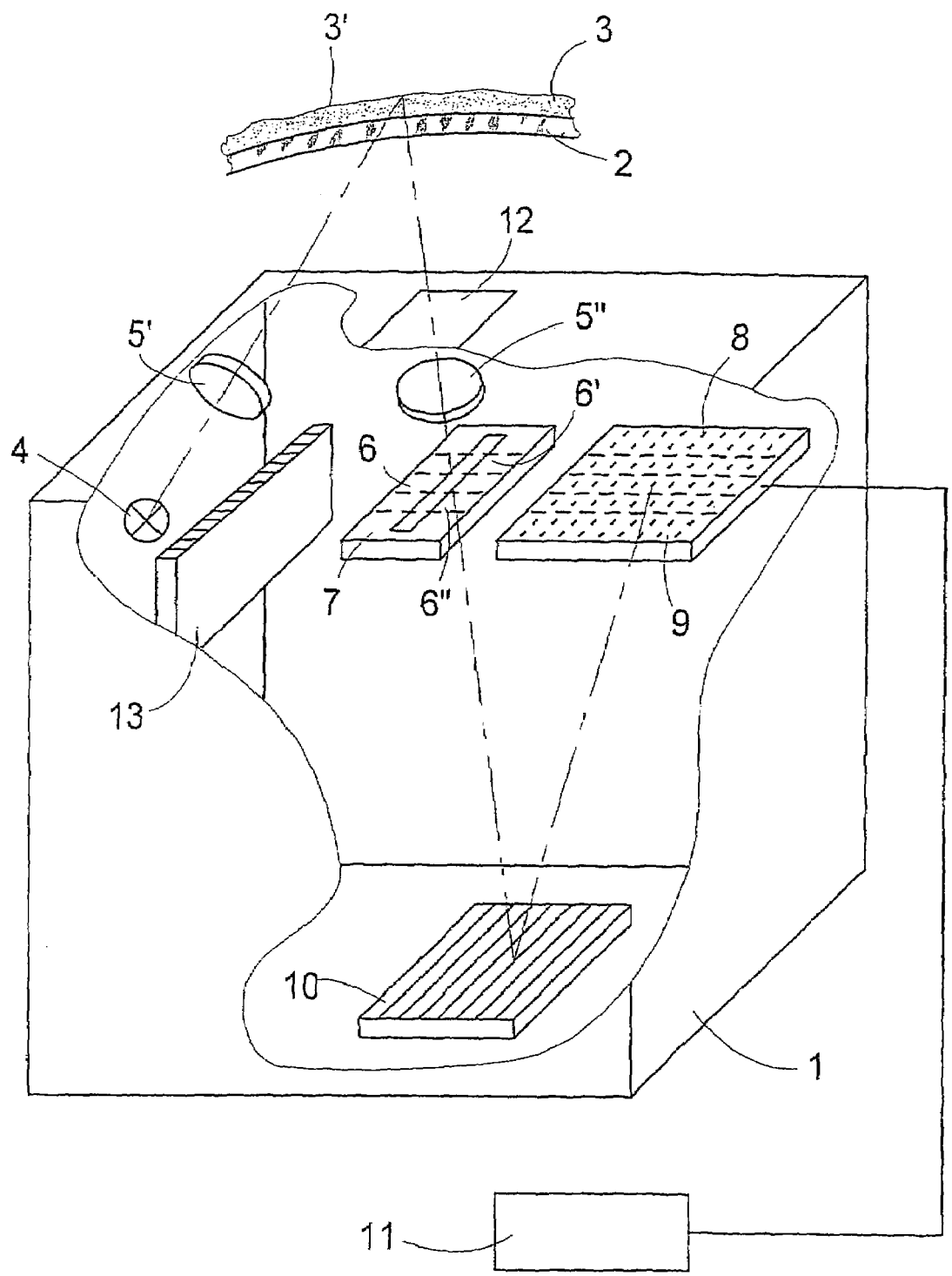
FIG. 1 is a schematic illustration of an arrangement according to the invention.

The arrangement shown in FIG. 1 for detecting coatings and determining their characteristics on surfaces, particularly coatings of water, ice and dirt on objects and in structural component parts of vehicles is basically a spectrometer. This arrangement comprises a housing 1. For the purpose of illuminating a coating 3 which is located on a transparent or opaque object 2, e.g., a windshield of a vehicle or a window pane, the housing 1 contains a light source 4, which emits radiation, and imaging optics which advantageously comprise a plurality of separate optical elements 5' and 5" for imaging the light source 4 along the coating 3 to be analyzed onto a larger or smaller limited portion 6 of the entrance slit 7.

When the distance between the coating 3 and the arrangement changes, which is usually the case in practice, it is necessary to image the light source 4 on the entrance slit 7 by means of a plurality of optical elements 5' and 5" in a telecentric beam path. Otherwise, the changes in distance and therefore also changes in the imaging sharpness can be mistaken for a roughness of the coating 3. Accordingly, in the arrangements according to FIGS. 1 and 2, the light source 4 is collimated, i.e., imaged to infinity, by the optical element 5'.

A focusing of the beam path on the entrance slit 7 is then carried out by the other optical element 5". Lenses and mirrors can be provided as optical elements 5' and 5".

An imaging grating 10, e.g., a holographic grating, is likewise arranged in the housing 1 for imaging the entrance slit 7 on a two-dimensional detector unit 8 comprising detector elements 9, e.g., CCD elements or CMOS elements, which are arranged in a matrix. The detector unit 8 is connected to an evaluating unit 11 in such a way that the signals of every individual detector element 9 can be prepared and processed in this evaluating unit 11.

As can be seen from FIG. 1, the coating 3 to be analyzed is illuminated through the object 2 supporting it. The light reflected by the surface 3' passes through an entrance window 12 of the housing 1 and is imaged onto the entrance slit 7 through the imaging optics 5.

Shielding members 13 are arranged inside the housing 1 so as to safely prevent the light of the light source 4 from influencing the imaging of the entrance slit 7 on the detector unit 8 through the grating 10 and to prevent corruption of the measurement results.

Figure 2:
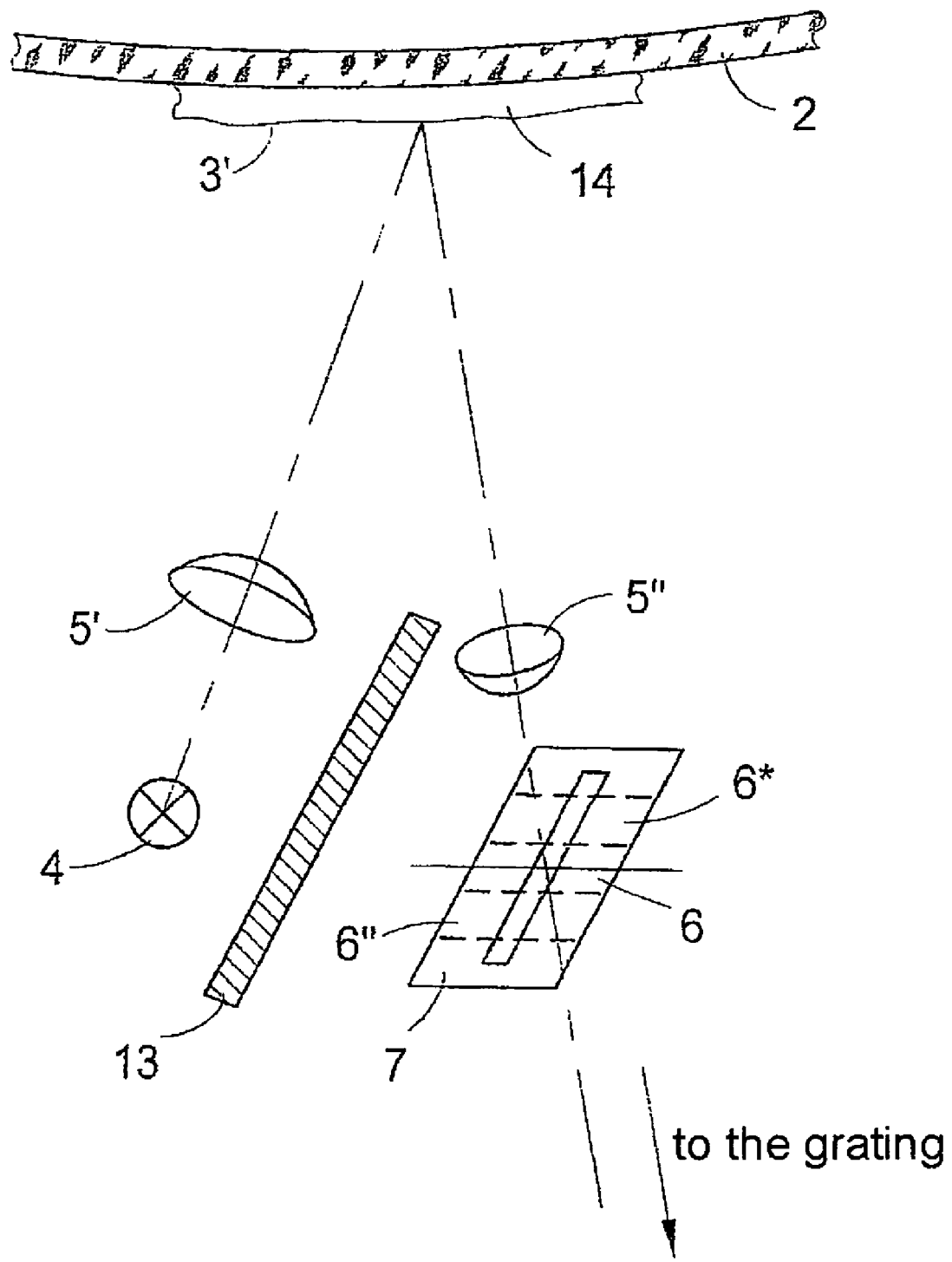
FIG. 2 is a schematic illustration of an arrangement according to the invention with incident illumination of the coating.

The arrangement which is shown schematically in FIG. 2 has the same components and subassemblies as the arrangement according to FIG. 1. Accordingly, the same reference numbers are used for members having identical functions. A coating 14 located on the object 2 is illuminated by incident light with the arrangement shown in FIG. 2. As in the arrangement according to FIG. 1, the light reflected by the surface 14' is directed to the entrance slit 7 and is imaged on the detector unit 8 (not shown in FIG. 2 for the sake of simplicity) through a holographic grating.

Figure 3:
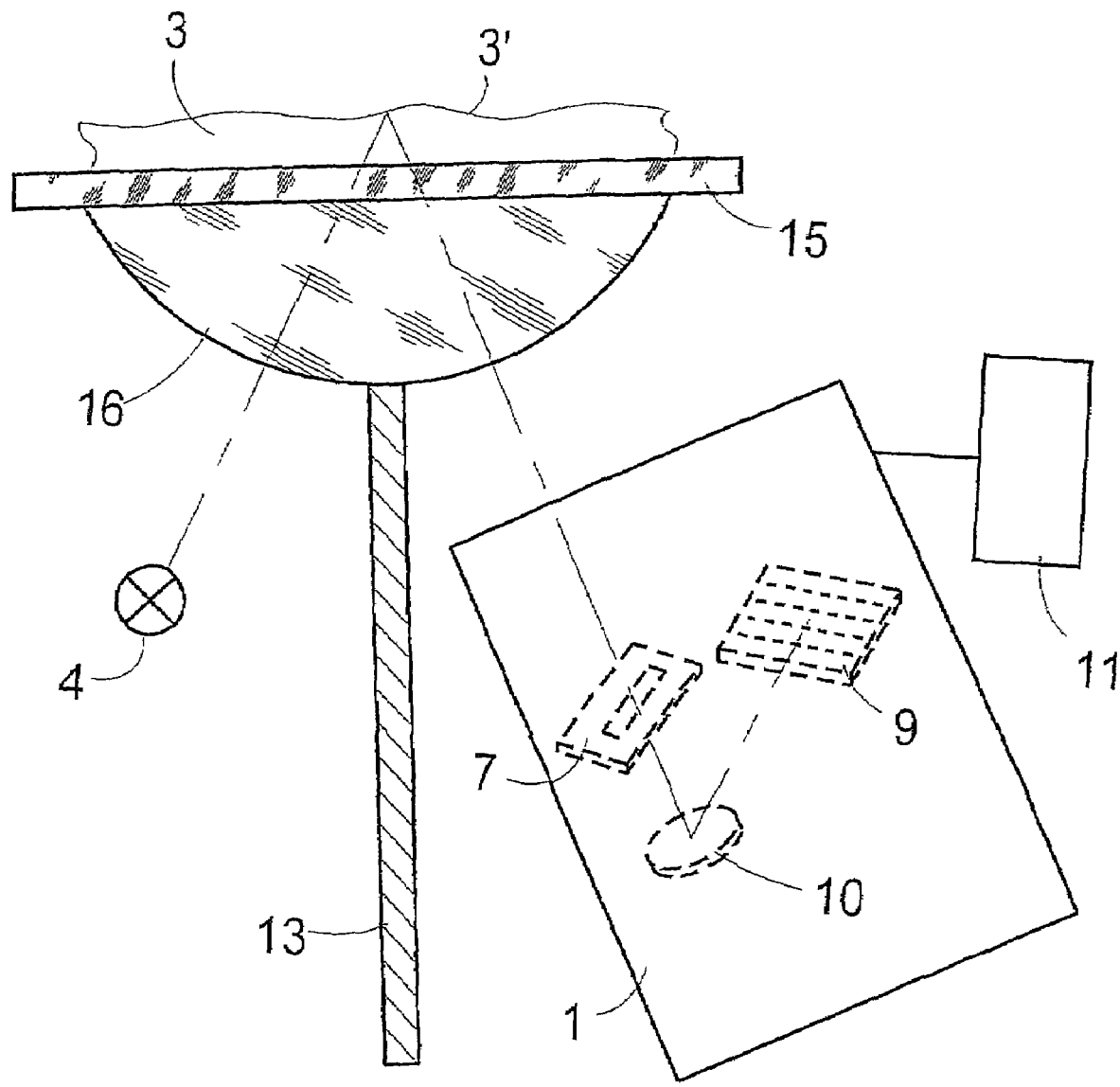
FIG. 3 shows an arrangement which is arranged on a transparent pane.

In order to detect and determine the characteristics of coatings with the arrangements according to FIGS. 1 to 3, the light source 4 is imaged on the entrance slit 7 over the coating 3; 14 to be analyzed (FIG. 2) through the imaging optics comprising elements 5'; 5" or through the lens 16 (FIG. 3). The light is influenced by the surface 3' or 14' of the respective coating 3 or 14. Depending on the properties (roughness) of the exposed surface 3' or 14' of the coating 3 or 14, only the portion 6 of the entrance slit 7 or, in the presence of roughness, another portion 6'; 6" on either side of the portion 6 is illuminated. In case of a smooth surface 3' or 14', only portion 6 of the entrance slit 7 is illuminated.

In order to obtain the spectrum, the signals of the detector elements (pixels) 9 belonging to a wavelength $\lambda$ are summed, as is conventional. The width and position of the spectrum stripes on the detector unit 8 are also calculated, e.g., by adding the signal values of all of the detector elements 9 in the dispersion direction. The width and position (location) of the center of gravity transverse to the dispersion direction are then calculated and values for the roughness of the surface 3' or 14' of the coating 3 or 14 to be analyzed are accordingly determined.

With the arrangement and the method carried out by means of the arrangement, not only is it possible to determine the composition and the thickness of the coating 3'; 14' in that the signals generated by the detector elements 9 are correspondingly evaluated and further processed in the evaluating unit 11, but the roughness of the surface 3' or 14' of the coating 3 or 14 can also be tested and determined based on the different dispersions of light or reflections.

The output signals of every individual detector element 9 are fed to the evaluating unit 11 and, by adding the signal values in the dispersion direction which are associated with a wavelength $\lambda$, the chemical composition and the thickness of the coating 3' or 14' are given based on known methods. Adding the signal values of the detector elements 9 in direction of the wavelength λ, that is, transverse to the dispersion direction, provides indications and measurements of the roughness of the surface 3' or 14' of the analyzed coating 3 or 14. A narrowly distributed sum indicates a smooth coating surface and a broadly distributed sum is characteristic of a rough surface.

In a highly simplified view, FIG. 3 shows another embodiment form of the arrangement which is arranged, for example, at a transparent windshield 17 of a vehicle. The illumination of a sharply defined area of the coating 3 to be analyzed through the light source 4 and the imaging of the light source 4 on the entrance slit 7 (shown in dashes) in the interior of the housing 1 of the arrangement are carried out through a shared lens 16. The light bundle emitted by the light source 4 traverses the windshield 15 and the coating 3 and is reflected at its surface 3' and imaged on the entrance slit 7 through the lens 16. Collimating and focusing of the imaging beam path are carried out through the shared lens 16. The light reaches the imaging grating 10 through the entrance slit 7 and is imaged on the detector unit 8 from the latter. The data supplied by the detector unit 8 are fed to the evaluating unit 11 and further processed therein. As was already mentioned in connection with the description referring to FIGS. 1 and 2, a shielding member 13 is provided in order to prevent the illumination beam path from influencing the imaging beam path.

By means of the arrangement according to the invention, the position of the coating 3 to be analyzed, that is, of the actual object to be measured, can also be determined from the position and location of the stripe imaged on the detector unit 8.

While the foregoing description and drawings represent the present invention, it will be obvious to those skilled in the art that various changes may be made therein without departing from the true spirit and scope of the present invention.

REFERENCE NUMBERS 1 housing
2 object
3 coating
3' surface
4 light source
5 imaging optics
5'; 5" optical element
6 portion
6'; 6" portion
7 entrance slit
8 detector unit
9 detector element
10 grating
11 evaluating unit
12 entrance window
13 shielding member
14 coating
15 windshield
16 lens

The invention claimed is:

1. An arrangement for detecting coatings that are arranged on surfaces of structural components parts and for determining the chemical characteristics and surface properties of these coatings, comprising:
    a light source for illuminating a coating to be analyzed on the surface of the structural component part;
    optical elements for imaging the light source on an entrance slit over the surface of the coating to be analyzed;
    a grating which images light from the entrance slit on a two-dimensional detector unit in a wavelength-dependent manner; and
    an evaluating unit being electrically connected to the detector unit for evaluating and processing signals supplied by irradiated detector elements of the detector unit, the evaluating unit being arranged to determine measurement values for the roughness of the surface of the analyzed coating from the breadth of the irradiated area on the detector unit.

2. The arrangement according to claim 1, wherein the detector elements are arranged in a matrix.

3. The arrangement according to claim 2, wherein the detector elements are CCD elements or CMOS elements.

4. A method for detecting coatings that are arranged on surfaces of structural component parts and for determining the chemical characteristics and the surface properties of the coatings with the arrangement according to claim 1, comprising the following method steps:
    illuminating the coating which is located on the surface of the structural component part and which is to be analyzed by a light source;
    imaging the light source on an entrance slit over the surface of the coating, which surface is to be analyzed and which reflects and/or scatters the light;
    imaging light from the entrance slit in a wavelength-dependent manner upon a two-dimensional detector unit by a grating, the detector unit comprising detector elements arranged in a matrix such that a broader or narrower two-dimensional area of the detector unit is irradiated depending upon the properties or roughness of the surface of the coating; and
    evaluating the signals of the irradiated detector elements and determining measurement values for the roughness of the surface of the analyzed coating from the breadth of the irradiated area on the detector unit and outputting the measurement values.

5. The method according to claim 4, wherein the illumination of the coating to be analyzed is carried out with transmitted light or incident light.

* * * * *